(12) United States Patent
Widenmeyer et al.

(10) Patent No.: US 10,690,612 B2
(45) Date of Patent: Jun. 23, 2020

(54) SENSOR FOR MEASURING THE CARBON DIOXIDE CONCENTRATION IN A GAS MIXTURE, AND METHOD FOR MANUFACTURE THEREOF

(71) Applicant: Robert Bosch GmbH, Stuttgart (DE)

(72) Inventors: Markus Widenmeyer, Schoenaich (DE); Richard Fix, Weil im Schoenbuch (DE); Martin Schreivogel, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 220 days.

(21) Appl. No.: 15/535,496

(22) PCT Filed: Oct. 26, 2015

(86) PCT No.: PCT/EP2015/074747
§ 371 (c)(1),
(2) Date: Jun. 13, 2017

(87) PCT Pub. No.: WO2016/102103
PCT Pub. Date: Jun. 30, 2016

(65) Prior Publication Data
US 2017/0343503 A1 Nov. 30, 2017

(30) Foreign Application Priority Data

Dec. 22, 2014 (DE) .................. 10 2014 226 810

(51) Int. Cl.
*G01N 27/22* (2006.01)
*G01N 27/00* (2006.01)
*G01N 33/00* (2006.01)

(52) U.S. Cl.
CPC ......... *G01N 27/227* (2013.01); *G01N 27/002* (2013.01); *G01N 27/221* (2013.01);
(Continued)

(58) Field of Classification Search
CPC .. G01N 27/227; G01N 27/002; G01N 27/221; G01N 27/226; G01N 33/004; G01N 2027/222
(Continued)

(56) References Cited

U.S. PATENT DOCUMENTS 3,802,268 A * 4/1974 Thoma ................. G01N 27/223
361/286
5,124,021 A * 6/1992 Kaneyasu ............ G01N 27/417
204/425

(Continued)

FOREIGN PATENT DOCUMENTS

| DE | 2 221 656 | 11/1972 |
|---|---|---|
| EP | 0 947 829 A1 | 10/1999 |
| KR | 20050058795 A * | 6/2005 |

OTHER PUBLICATIONS

Translate KR-20050058795-A (Year: 2005).*

(Continued)

*Primary Examiner* — Natalie Huls
*Assistant Examiner* — Monica S Young
(74) *Attorney, Agent, or Firm* — Maginot, Moore & Beck LLP

(57) ABSTRACT

A sensor is configured to measure the carbon dioxide concentration in a gas mixture. The sensor has a dielectric layer arranged between a layer-like first electrode and a layer-like second electrode. The second electrode is a composite electrode that has at least one carbonate and/or one phosphate as first material and at least one metal as second material. This sensor can be manufactured by a method comprising applying a layer-like first electrode to a substrate, applying a dielectric layer to the first electrode, and applying a layer-like second electrode to the dielectric layer. The second electrode is applied as a composite electrode that has at least one carbonate and/or one phosphate as first
(Continued)

material and has at least one second material that has an electrical conductivity of more than 10-2 S/m.

13 Claims, 4 Drawing Sheets

(52) U.S. Cl.
CPC ......... *G01N 27/226* (2013.01); *G01N 33/004* (2013.01); *G01N 2027/222* (2013.01)

(58) Field of Classification Search
USPC .............................................................. 73/31
See application file for complete search history.

(56) References Cited

U.S. PATENT DOCUMENTS

| | | | | |
|---|---|---|---|---|
| 5,958,340 A * | 9/1999 | Meyer | G01N 33/004 | 205/783.5 |
| 5,993,624 A * | 11/1999 | Matsubara | G01N 27/12 | 204/421 |
| 7,495,300 B2 * | 2/2009 | Gardner | G01N 27/128 | 257/252 |
| 2003/0064604 A1 | 4/2003 | Umeda | H01L 21/31691 | 438/745 |
| 2005/0100478 A1 * | 5/2005 | Harvey | G01N 27/4163 | 422/83 |
| 2005/0129573 A1 * | 6/2005 | Gabriel | B82Y 10/00 | 422/400 |
| 2005/0245836 A1 * | 11/2005 | Star | B82Y 10/00 | 257/253 |
| 2006/0070890 A1 * | 4/2006 | Itoh | G01N 27/4075 | 205/775 |
| 2006/0091010 A1 * | 5/2006 | Komatsu | G01N 27/4074 | 204/427 |
| 2006/0096871 A1 * | 5/2006 | Manoukian | G01N 27/4074 | 205/782 |
| 2007/0048180 A1 * | 3/2007 | Gabriel | B82Y 15/00 | 422/400 |
| 2007/0048181 A1 * | 3/2007 | Chang | B82Y 15/00 | 422/400 |
| 2008/0221806 A1 * | 9/2008 | Bryant | G01N 27/127 | 702/22 |
| 2009/0039346 A1 * | 2/2009 | Nishiyama | H01L 31/02168 | 257/43 |
| 2009/0095626 A1 * | 4/2009 | Dutta | G01N 27/4074 | 204/424 |
| 2010/0314700 A1 * | 12/2010 | Park | G01N 27/128 | 257/414 |
| 2011/0226042 A1 * | 9/2011 | Yu | G01N 27/4074 | 73/31.05 |
| 2012/0263870 A1 * | 10/2012 | Hunter | G01N 27/4074 | 427/125 |
| 2018/0038816 A1 * | 2/2018 | Hsiao | G01N 27/125 | |
| 2018/0372662 A1 * | 12/2018 | Boudaden | G01N 27/126 | |
| 2019/0282143 A1 * | 9/2019 | Kamath | A61B 5/6848 | |

OTHER PUBLICATIONS

International Search Report corresponding to PCT Application No. PCT/EP2015/074747 dated Apr. 1, 2016 (German and English language document) (7 pages).

Plonka et al.; Impact of the top-electrode material on the permittivity of single-crystalline Ba0.7Sr0.3TiO3 thin films, Applied Physics Letters, 2005, pp. 202908-1 to 202908-3, vol. 86, American Institute of Physics.

Ostrick et al.; Adsorbed water as key to room temperature gas-sensitive reactions in work function type sensors: the carbonate-carbon dioxide system; Sensors and Actuators B, 1999, pp. 115-119, vol. 57, Elsevier Science S.A.

Lundström et al.; Twenty-five years of field effect gas sensor research in Linköping; Sensors and Actuators B, 2007, pp. 247-262, vol. 121, Elsevier B.V., www.sciencedirect.com.

* cited by examiner

SENSOR FOR MEASURING THE CARBON DIOXIDE CONCENTRATION IN A GAS MIXTURE, AND METHOD FOR MANUFACTURE THEREOF

This application is a 35 U.S.C. § 371 National Stage Application of PCT/EP2015/074747, filed on Oct. 26, 2015, which claims the benefit of priority to Serial No. DE 10 2014 226 810.9, filed on Dec. 22, 2014 in Germany, the disclosures of which are incorporated herein by reference in their entireties.

The disclosure relates to a sensor for measuring the carbon dioxide concentration in a gas mixture, particularly in ambient air. The disclosure furthermore relates to a method for producing a sensor according to the disclosure.

BACKGROUND

The measurement of gas concentrations is gaining increasing importance in the field of consumer electronics (CE) as well as building safety technology and medical technology. This applies in particular for networked devices (IoTS). There is particular interest in the development of small economical sensors with a low power consumption, which can be integrated in large production numbers into existing devices. To this end, there are many different approaches. Mention may in this case be made particularly of resistive sensors, the conductivity variation of which as a function of the gas atmosphere is read out, and various types of field-effect transistors which detect the work function variation of the electrode material used. The former in principle presuppose a relatively good electrical conductivity of the gas-sensitive materials. The latter have the disadvantage of elaborate processing and relatively high power consumption, if heating is necessary. This is problematic in particular when the sensor elements are intended to be applied onto micro-heating plates, such as those which may for example be used in cell phones.

One important target gas for CE applications is carbon dioxide ($CO_2$), for example in order to monitor the room air quality. Until now, infrared sensors which require a relatively large installation space have predominantly been used for $CO_2$ measurement.

Solid electrolyte components, for example barium carbonate/gold electrodes, which operate at high temperatures, are also used.

It is known from Ostrick B., Mühlsteff J., Fleischer M., Meixner H., Doll T., Kohl C.-D., Absorbed water as key to room temperature gas-sensitive reactions in work function type gas sensors: the carbonate carbon dioxide system. Sens. Actuat. B-Chem. 1999; 57: 115-119, that barium carbonate already exhibits significant work function variations as a function of the $CO_2$ partial pressure even at temperatures below 100° C. The readout of this effect with the aid of suspended-gate field-effect transistors is described in EP 0 947 829 A1. Such field-effect transistors have a dielectric layer which is arranged between two electrodes. One of these electrodes is configured as a composite electrode. Such a sensor structure is in principle also used for detecting other analytes. For example, a moisture sensor which is known from DE 2 221 656 A1 has a similar structure.

R. Plonka, R. Dittmann, N. A. Pertsev, E. Vasco, R. Waser, Impact of the top-electrode material on the permittivity of single-crystalline $Ba_{0.7}Sr_{0.3}TiO_3$ thin films, Appl. Phys. Lett. 86, 202909 (2005) describes the dependency of the impedance of a thin-film capacitor, which contains $Ba_{0.7}Sr_{0.3}TiO_3$ as a dielectric, on the material of the electrodes used.

SUMMARY

The sensor according to the disclosure for measuring the carbon dioxide concentration in a gas mixture, particularly in ambient air, has a dielectric layer which is arranged between a first electrode in the form of a layer and a second electrode in the form of a layer. According to the disclosure, a dielectric layer is intended to mean a layer which may consist of only a single layer or a plurality of sublayers, in which case the sublayers may have a different composition and/or structure. The second electrode is a composite electrode which comprises at least one carbonate and/or phosphate as the first material of the composite electrode and at least one second material of the composite electrode. The second electrode changes its work function as a function of the $CO_2$ concentration of the gas mixture. The disclosed structure of the sensor is extremely compact and relatively easy to process. This offers the possibility of integrating the sensor in a device having very restricted installation space with low power consumption. Furthermore, a suspended-gate arrangement is not necessary. This saves on very elaborate processing as well as installation space and thermal mass.

The thickness of the dielectric layer is preferably at most 10 µm. The thickness of the first electrode is preferably at most 5 µm. The thickness of the second electrode is preferably at most 100 µm. In this way, the dielectric layer is formed as a dielectric thin film which is embedded between two thin electrodes. This leads to a metal/insulator/metal (MIM) structure. An MIM structure with bias-dependent permittivity makes it possible to use standard evaluation methods for capacitance measurement, as employed in MEMS (microelectromechanical systems) technology. The thin film preferably changes its electrical properties, i.e. its permittivity or impedance, as a function of an externally applied electric field, and therefore the bias voltage. Particularly preferably, it can have its polarity reversed at least locally so that in the polarized state it has a relative permittivity that is less by a factor greater than or equal to 1.001, more particularly preferably greater than or equal to 1.1, than in an unpolarized state. The conductivity of the dielectric layer preferably lies in the range of from $10^{-8}$ S/m to $10^{-3}$ S/m, in order to ensure sufficient electrical insulation between the two electrodes.

The dielectric layer consists of a ferroelectric, i.e. of a material whose unit cells, because of the lattice structure, have an electrical dipole moment which can be aligned in an electric field. In particular, the ferroelectric is barium titanate ($BaTiO_3$), lead zirconate titanate ($Pb(Zr_x Ti_{1-x})O_3$, PZT) or barium strontium titanate ($Ba_x Sr_{1-x} TiO_3$, BST). Ferroelectrics can be used in the sensor element according to the disclosure only below their ferroelectric Curie temperature. For thin layers, however, their phase transition extends over a temperature range which is so wide that ferroelectric properties are still observed even at relatively high temperatures. Preferably, the dielectric has a coercive field strength of less than 3 V/layer thickness, in order to allow rapid polarity reversal in an alternating electric field. If the surface potential or work function of at least one of the electrodes changes, this acts like a bias offset and leads to a measurable change in the impedance of the sensor according to the disclosure.

The carbonate is selected from the list consisting of lithium carbonate, sodium carbonate, magnesium carbonate, calcium carbonate, strontium carbonate, barium carbonate, manganese carbonate, cobalt carbonate, nickel carbonate, copper carbonate and mixtures of a plurality of these carbonates. Particularly preferred is barium carbonate, which exhibits large surface potential variations as a function of the $CO_2$ concentration in the gas mixture at temperatures of between 0° C. and 100° C. and with usual relative air humidities of at least 10%.

The phosphates are apatites and hydroxyapatites which contain at least one of the cations $Ca^{2+}$, $Sr^{2+}$ or $Ba^{2+}$.

The second electrode preferably has a gas permeability so high that saturation of the signal is reached in at most 30 minutes, when it is applied according to Lundström I., Sundgren H., Winquist, F., Eriksson M., Krantz-Rückler C., Lloyd-Spetz A., Sensors and Actuators B 121 (2007) 247-262 onto the gate of a gas-sensitive field-effect transistor and is exposed to a carbon dioxide atmosphere. This means that its ratio between porosity and thickness is selected in such a way that a good interaction with the gas mixture can be achieved.

The second material is in particular selected from platinum, gold, silver, copper, aluminum, nickel, zinc, indium tin oxide (ITO), aluminum-doped zinc oxide (AZO), or an alloy or mixture of a plurality of these elements or compounds. The material of the first electrode is preferably selected from the same materials as the material of the second electrode. These noble metals and noble metal alloys do not react with usual atmospheric constituents in normal concentration, or do not react to a substantial extent, so that aging of the electrodes is prevented. The two electrodes are used together in order to impose an electric field in the sensor according to the disclosure, or to influence a reaction between the carbonate and/or the phosphate and carbon dioxide contained in the gas mixture.

The first electrode is preferably applied on a membrane of a micro-heating plate as a substrate. This makes it possible to vary the operating temperature of the second electrode of the sensor according to the disclosure, for example between ambient temperature and 300° C. A particularly advantageous operating temperature is, for example 50° C.

It is particularly preferred for the first electrode to be configured as a heater of the micro-heating plate. In this way, a separate heating element, for example in the form of a platinum meander, can be obviated, and particularly good heat transfer to the dielectric layer and the second electrode is possible.

In one embodiment of the sensor according to the disclosure, the first material is arranged between the second material and the dielectric layer. In this way, in the second electrode, the first material may form a sublayer which touches the dielectric and the second material may form a further sublayer, which protects the first material, on the side of the first material facing away from the dielectric.

In another embodiment of the sensor according to the disclosure, the second material is present in the form of particles which are coated with the first material and/or contain the first material in pores of the particles. This allows a high surface interaction between the first material and the second material.

In yet another embodiment of the sensor according to the disclosure, the second electrode comprises a mixture of particles of the first material and particles of the second material. Such a second electrode is simple to produce but nevertheless allows sufficient contact between the first material and the second material.

The method according to the disclosure for producing a sensor for measuring the carbon dioxide concentration in a gas mixture, in particular a sensor according to the disclosure, comprises the following steps:
applying a first electrode in the form of a layer onto a substrate,
applying a dielectric layer onto the first electrode, and
applying a second electrode in the form of a layer onto the dielectric layer.

The second electrode is applied as a composite electrode which comprises at least one carbonate, which is selected from $Li_2CO_3$, $Na_2CO_3$, $MgCO_3$, $CaCO_3$, $SrCO_3$, $BaCO_3$, $MnCO_3$, $CoCO_3$, $NiCO_3$, $CuCO_3$ or a mixture of a plurality of these carbonates, and/or a phosphate, which is selected from an apatite and/or a hydroxyapatite which contains at least one of the cations $Ca^{2+}$, $Sr^{2+}$ or $Ba^{2+}$, as the first material of the composite electrode and at least one second material of the composite electrode, which is selected from platinum, gold, silver, copper, indium tin oxide, aluminum-doped zinc oxide, or an alloy or mixture of a plurality of these elements or compounds. The deposition of the electrodes and of the dielectric layer may, for example, be carried out wet-chemically from a solution, from a suspension or from a colloidal solution, or physically, in particular by means of CVD (chemical vapor deposition), MOCVD (metal organic chemical vapor deposition), sputtering, ALD (atomic layer deposition) or PLD (physical layer deposition). If porosity of the first material and/or of the second material is desired, this may in particular be achieved by suitable selection of the process parameters or by an additional heat-treatment step.

If the second electrode contains a carbonate, this may in particular be applied by applying, during the application of the second electrode, at least one oxide which is subsequently reacted with carbon dioxide to form the at least one carbonate. Thus, for example, barium oxide may first be deposited and subsequently reacted to form barium carbonate.

In one embodiment of the method according to the disclosure, during the application of the second electrode, in a first step the first material is deposited on the dielectric layer and a first sublayer of the second electrode is thereby formed. In a second step, the second material is deposited on the first material and a second sublayer is thereby formed. In this way, a sublayer of the carbonate and/or phosphate, which is covered by a metallic front electrode, is formed on the dielectric.

In another embodiment of the method according to the disclosure, during the application of the second electrode, in a first step the second material is deposited in the form of particles on the dielectric layer, and in a second step the first material is deposited on the surface of the second material and/or in pores of the second material. Suitable methods for depositing the first material, or a precursor of the first material, for example an oxide, in cavities of the porous second material are in particular CVD, MOCVD, ALD, or wet-chemical methods.

In yet another embodiment of the method according to the disclosure, the first material and the second material are deposited simultaneously on the dielectric layer during the application of the second electrode. In this way, in particular, it is possible to use wet-chemical methods in which, for example, alkali metal salts or alkaline-earth metal salts are added to a salt solution or colloidal solution of the second material. During suitable drying or heat-treatment, in the presence of oxygen and carbon dioxide, an alkali metal carbonate or alkaline-earth metal carbonate is formed on the surface of the second material, or in cavities between particles of the second material.

For contacting of the sensor, after the end of the method according to the disclosure, the first electrode and the second electrode are connected to evaluation electronics, in particular by means of corresponding leads. The electronics may, in particular, be configured in order to read out the impedance or capacitance of the sensor as a function of the gas mixture.

BRIEF DESCRIPTION OF THE DRAWINGS

Exemplary embodiments of the disclosure are represented in the drawings and will be explained in more detail in the following description.

DETAILED DESCRIPTION

Figure 1:
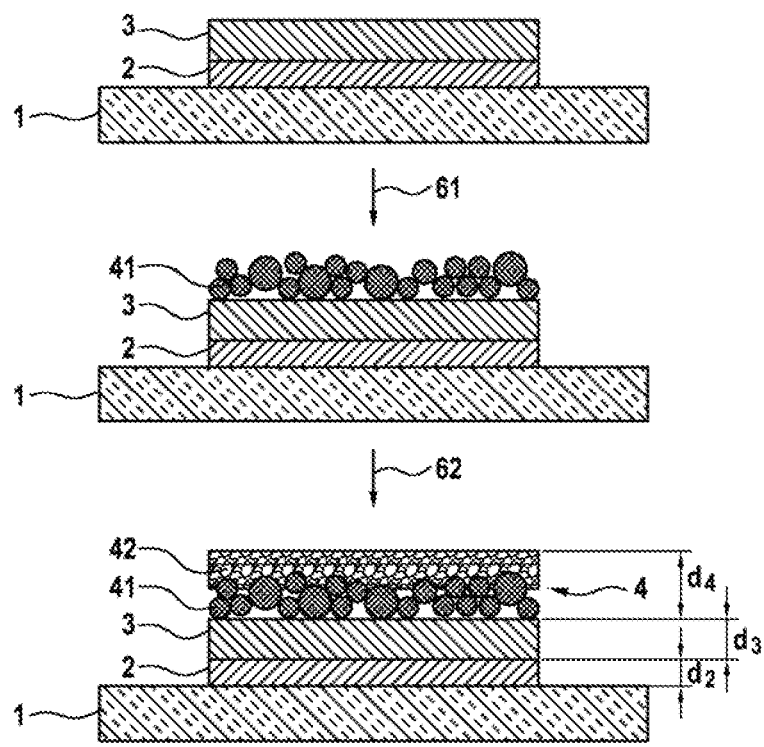
FIG. 1 schematically shows the production of a sensor for measuring the carbon dioxide concentration in a gas mixture in a first exemplary embodiment of the disclosure.

In a first exemplary embodiment of the disclosure, which is represented in FIG. 1, a first electrode 2 made of platinum is deposited on a substrate 1, which is an exposed membrane of a micro-heating plate, for example by means of CVD in the middle of the substrate 1. On this electrode, a dielectric layer 3 of lead zirconate titanate is deposited by means of CVD. In order to apply a second electrode 4 onto the dielectric layer 3, in a first step 61 a first porous sublayer 41 of barium carbonate is applied by means of CVD. In a second step 62, a porous second sublayer 42 of platinum is likewise applied onto the first sublayer 41 by means of sputtering. The two sublayers 41, 42 together form the second electrode 4. The first electrode 2 has a thickness $d_2$ of 100 nm. The dielectric layer 3 has a thickness $d_3$ of 500 nm. The second electrode 4 has a thickness $d_4$ of 200 nm. The first electrode 2, the dielectric layer 3 and the second electrode 4 therefore form a thin-film MIM structure.

Figure 2:
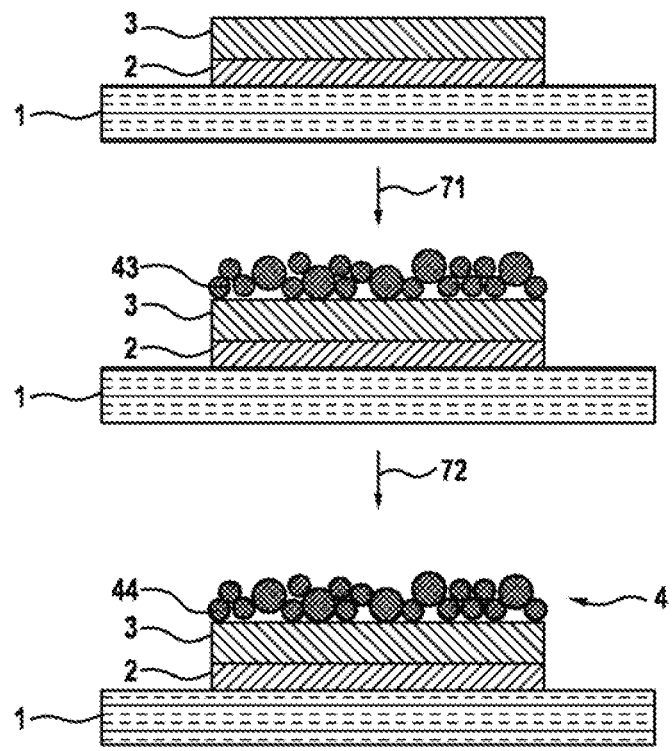
FIG. 2 schematically shows the production of a sensor for measuring the carbon dioxide concentration in a gas mixture in a second exemplary embodiment of the disclosure.

A second exemplary embodiment of the disclosure is represented in FIG. 2. First, in the same way as in the exemplary embodiment, a structure consisting of a substrate 1, a first electrode 2 and a dielectric layer 3 is provided. Then, in the first step 71, platinum is deposited from a colloidal solution onto the dielectric layer 3, so as to produce a layer of porous particles 43 on the dielectric layer 3. Subsequently, in a second step 72, barium oxide is first deposited on the surface and in the pores of the particles 43 by means of CVD and subsequently reacted by means of carbon dioxide to form barium carbonate. In this way, a barium carbonate layer is produced on and in the particles 43, so that coated particles 44 are obtained.

Figure 3:
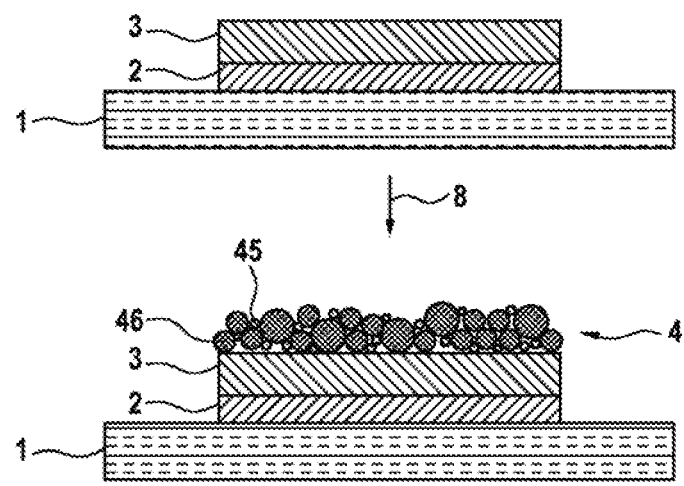
FIG. 3 schematically shows the production of a sensor for measuring the carbon dioxide concentration in a gas mixture in a third exemplary embodiment of the disclosure.

In a third exemplary embodiment, which is represented in FIG. 3, a structure consisting of the substrate 1 of the first electrode 2 and of the dielectric layer 3 is first provided as in the first and second exemplary embodiments. Subsequently, all the materials of the second electrode 4 are deposited on the dielectric layer 3 in a single step 8. This is done wet-chemically by adding barium chloride to a colloidal platinum solution. During drying in the presence of oxygen and carbon dioxide, barium carbonate 45 is then formed on the surface and in cavities between particles 46 of platinum.

Figure 4:
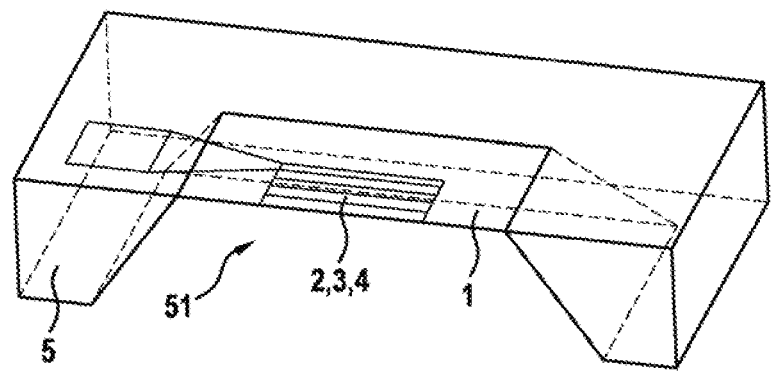
FIG. 4 shows the way in which the two electrodes and the dielectric layer of a sensor for measuring the carbon dioxide concentration in a gas mixture are arranged on a micro-heating plate in one embodiment of the disclosure.

FIG. 4 represents the way in which the substrate 1 is arranged as an exposed membrane in a micro-heating plate 5. The micro-heating plate 5 forms a cavity 51. The substrate 1 is arranged in such a way that the first electrode 2, the dielectric layer 3 and the second electrode 4 face away from the cavity 51. A heater plane (not represented) is placed centrally in the substrate 1, the first electrode 2 functioning as a heating element. The structure represented allows a power consumption of the sensor of much less than 100 mW even in continuous operation. Furthermore, because of the low thermal mass of the overall structure, rapid modulation at different operating temperatures is possible. A duty cycle of 1:10 may be achieved, and a measurement may be carried out within a very short time at different temperatures. This fact that adsorption and desorption reactions taking place on the second electrode 4 can be accelerated by continuous or pulsed heating is exploited in this way, and the response or regeneration times of the sensor can therefore be shortened.

Figure 5:
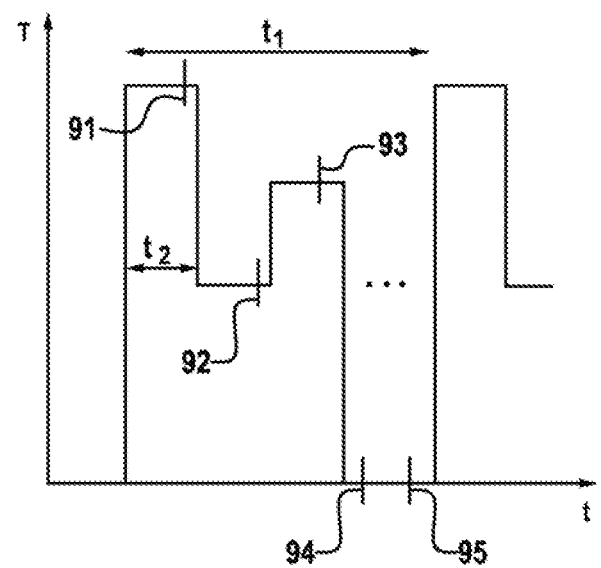
FIG. 5 shows a diagram of a setpoint temperature cycle during the operation of a sensor according to one embodiment of the disclosure.

FIG. 5 represents an exemplary setpoint temperature cycle of the sensor represented in FIG. 4. To this end, the setpoint temperature T is plotted against time t in a diagram. Between the start of two heating processes, a period $t_1$ of one second respectively elapses. The maximum setpoint temperature reached during the heating is maintained for a period $t_2$ of less than 50 ms. Subsequently, the setpoint temperature T is lowered, maintained at the lowered setpoint temperature T again for the period $t_2$, and lastly increased once more for a period $t_2$ to a setpoint temperature T which is higher but does not correspond to the setpoint temperature T initially reached, before the heating is turned off for the rest of the period $t_1$. Readouts 91, 92, 93, 94, 95 of the sensor according to the invention disclosure may be carried out at regular time intervals, so that at least one first readout 91 takes place at the maximum setpoint temperature T reached a second readout 92 at the lowered setpoint temperature T and a third readout 93 at the again increased setpoint temperature T.

The invention claimed is:
1. A sensor for measuring the carbon dioxide concentration in a gas mixture, the sensor comprising:
  a dielectric layer consisting of a ferroelectric and arranged between a first electrode in the form of a layer and a second electrode in the form of a layer, wherein:
  the second electrode is a composite electrode which includes a first material and at least one second material,
  the first material of the composite electrode comprises at least one carbonate, selected from $Li_2CO_3$, $Na_2CO_3$, $MgCO_3$, $CaCO_3$, $SrCO_3$, $BaCO_3$, $MnCO_3$, $CoCO_3$, $NiCO_3$, $CuCO_3$ or a mixture of a plurality of these carbonates, and/or a phosphate, selected from an apatite and/or a hydroxyapatite which contains at least one of the cations $Ca^{2+}$, $Sr^{2+}$ or $Ba^{2+}$, and
  the at least one second material of the composite electrode is selected from platinum, gold, silver, copper, indium tin oxide, aluminum-doped zinc oxide, or an alloy or mixture of a plurality of these elements or compounds, wherein the second material is present in the form of particles, the particles having one or more of a coating of the first material and the first material in pores of the particles.

2. The sensor as claimed in claim 1, wherein:
a thickness of the dielectric layer is at most 10 μm,
a thickness of the first electrode is at most 5 μm, and
a thickness of the second electrode is at most 100 μm.

3. The sensor as claimed in claim 1, wherein the first electrode is applied on a membrane of a micro-heating plate as a substrate.

4. The sensor as claimed in claim 3, wherein the first electrode is configured as a heater of the micro-heating plate.

5. The sensor as claimed in claim 1, wherein the first material is arranged between the second material and the dielectric layer.

6. The sensor as claimed in claim 1, wherein the second electrode comprises a mixture of particles of the first material and particles of the second material.

7. A sensor for measuring the carbon dioxide concentration in a gas mixture, the sensor comprising:
a dielectric layer consisting of a ferroelectric and arranged between and in direct contact with each of a first electrode in the form of a layer and a second electrode in the form of a layer, wherein:
the second electrode is a composite electrode which consists of a first material and at least one second material,
the first material of the composite electrode comprises at least one carbonate, selected from $Li_2CO_3$, $Na_2CO_3$, $MgCO_3$, $CaCO_3$, $SrCO_3$, $BaCO_3$, $MnCO_3$, $CoCO_3$, $NiCO_3$, $CuCO_3$ or a mixture of a plurality of these carbonates, and/or a phosphate, selected from an apatite and/or a hydroxyapatite which contains at least one of the cations $Ca^{2+}$, $Sr^{2+}$ or $Ba^{2+}$, and
the at least one second material of the composite electrode is selected from platinum, gold, silver, copper, indium tin oxide, aluminum-doped zinc oxide, or an alloy or mixture of a plurality of these elements or compounds.

8. The sensor as claimed in claim 7, wherein:
a thickness of the dielectric layer is at most 10 μm,
a thickness of the first electrode is at most 5 μm, and
a thickness of the second electrode is at most 100 μm.

9. The sensor as claimed in claim 7, wherein the first electrode is applied on a membrane of a micro-heating plate as a substrate.

10. The sensor as claimed in claim 9, wherein the first electrode is configured as a heater of the micro-heating plate.

11. The sensor as claimed in claim 7, wherein the first material is arranged between the second material and the dielectric layer.

12. The sensor as claimed in claim 7, wherein the second material is present in the form of particles, the particles having one or more of a coating of the first material and the first material in pores of the particles.

13. The sensor as claimed in claim 7, wherein the second electrode comprises a mixture of particles of the first material and particles of the second material.

* * * * *